United States Patent
Göbbel et al.

(10) Patent No.: US 6,916,964 B2
(45) Date of Patent: Jul. 12, 2005

(54) SELECTIVE HYDROGENATION OF OLEFINICALLY UNSATURATED CARBONYL COMPOUNDS

(75) Inventors: Hans-Georg Göbbel, Kallstadt (DE); Till Gerlach, Ludwigshafen (DE); Frank Funke, Mannheim (DE); Klaus Ebel, Lampertheim (DE); Signe Unverricht, Mannheim (DE); Gerd Kaibel, Lampertheim (DE)

(73) Assignee: BASF AG, Ludwigshafen (DE)

( * ) Notice: Subject to any disclaimer, the term of this patent is extended or adjusted under 35 U.S.C. 154(b) by 371 days.

(21) Appl. No.: 10/309,181

(22) Filed: Dec. 4, 2002

(65) Prior Publication Data

US 2003/0109758 A1 Jun. 12, 2003

(30) Foreign Application Priority Data

Dec. 7, 2001 (DE) ......................... 101 60 143

(51) Int. Cl.$^7$ .................. C07C 29/136; C07C 29/14; C07C 29/143; C07C 29/147
(52) U.S. Cl. .................. 568/881; 568/875; 568/876; 568/878; 568/880; 568/884; 568/885; 568/902; 568/903; 568/909.5
(58) Field of Search ................. 568/881, 875, 568/902, 909.5, 903, 876, 878, 880, 884, 885

(56) References Cited

U.S. PATENT DOCUMENTS

| 4,100,180 A | 7/1978 | Ichikawa et al. |
| 4,320,228 A | 3/1982 | Horner et al. |
| 5,939,589 A | 8/1999 | Kaibel et al. |

FOREIGN PATENT DOCUMENTS

| EP | 024 651 | 3/1981 |
| EP | 798 039 | 10/1997 |

OTHER PUBLICATIONS

XP-002253580,Jr.Cat.199, 73–84 (2001).
XP-002253581,Jr.Cat. 204, 450–459 (2001).
XP-002253582,Applied Catalysis A: General 196(2000) 93–102.
XP009015172,Research and Industry Bd. 17, Mar. 1972, Sieiten 11–12.
J.CHem. Tech.Biotechnol 1994, 60, 83–88, Neri et al.

*Primary Examiner*—Elvis O. Price
(74) *Attorney, Agent, or Firm*—Novak Druce & Quigg, LLP

(57) ABSTRACT

The present invention relates to a continuous process for the selective hydrogenation of olefinically unsaturated carbonyl compounds to give unsaturated alcohols in particular of citral to give a mixture of geraniol and nerol, in a reactor containing a liquid phase, in which at least one catalyst is suspended, and which can additionally contain a gas phase, wherein the liquid phase and, if present, the gas phase are passed through a device in the reactor having openings or channels.

11 Claims, 1 Drawing Sheet

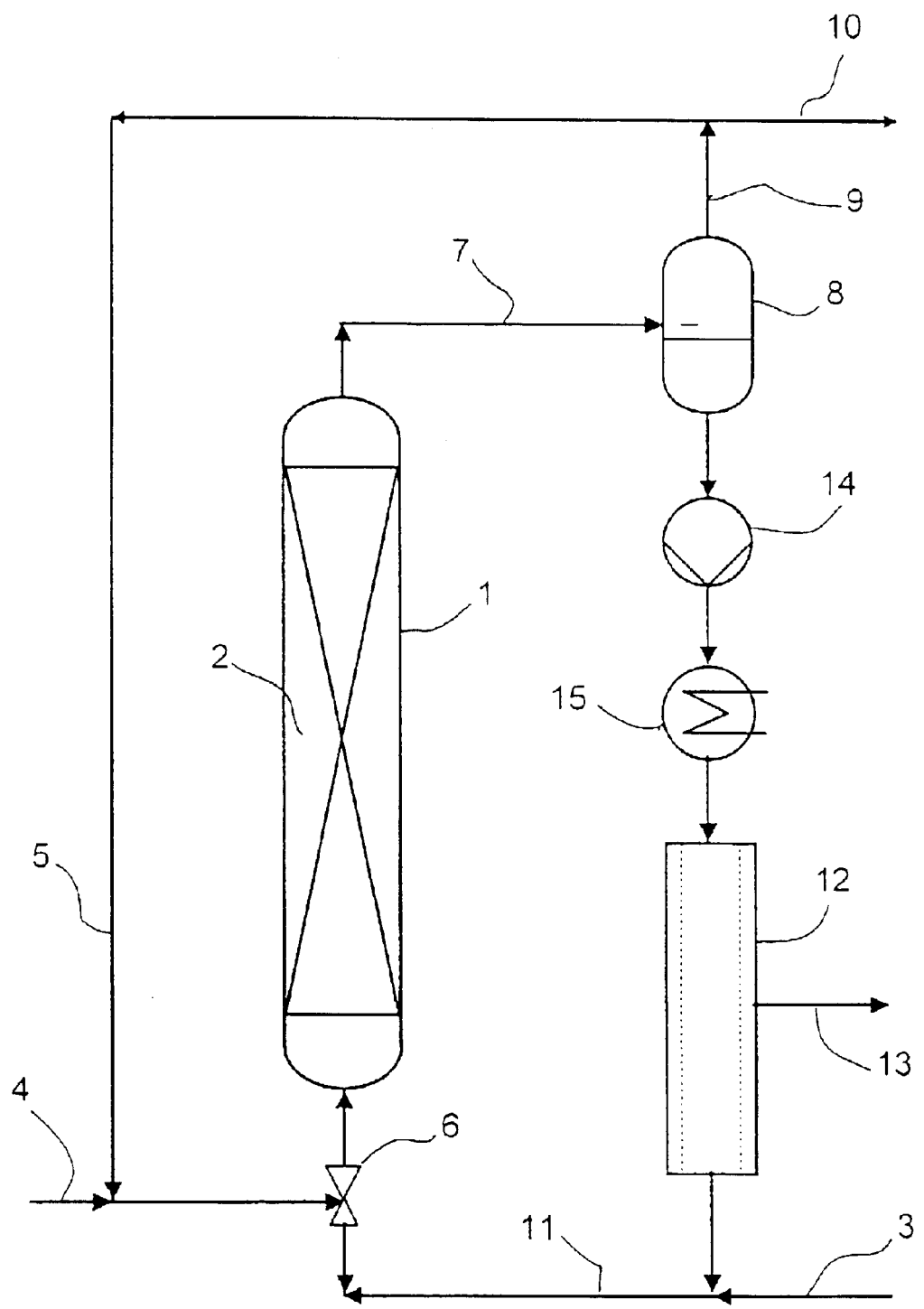

SELECTIVE HYDROGENATION OF OLEFINICALLY UNSATURATED CARBONYL COMPOUNDS

The present invention relates to a process for the selective hydrogenation of α,β-unsaturated carbonyl compounds to give unsaturated alcohols, in particular of citral to give a mixture of geraniol and nerol, in a reactor containing, in the absence or presence of a gas phase, a liquid phase holding at least one catalyst in suspension, which comprises passing the liquid phase and, if present, the gas phase through a device in the reactor having openings or channels.

Citral and the corresponding hydro-compounds find use as scents and are further used as starting materials in the synthesis of vitamins.

The prior art discloses various hydrogenation processes for α,β-unsaturated carbonyl compounds. It is very difficult to obtain high selectivities for the corresponding unsaturated alcohols. The hydrogenation of citral can lead to the hydrogenation of the olefinic double bonds as well as the aldehyde group, or only of the double bond conjugated to the aldehyde group, so that, as well as the unsaturated alcohols geraniol or nerol, by-products such as citronellol or citronellal can be formed.

U.S. Pat. No. 4,100,180 describes a batchwise process for the hydrogenation of unsaturated aldehydes to give unsaturated alcohols in the presence of a PtO/Zn/Fe catalyst. PtO powder is doped with Zn and Fe (suspension catalyst). The hydrogenation of citral at a citral conversion of 70% gives 3.2% citronellol. In the reaction effluents, up to 25 ppm of Fe and Zn compounds are found. If the catalyst is reused, small amounts of Fe and Zn compounds must be added.

EP 798 039 discloses a process for the conduction of a catalytic reaction in a reactor which contains a liquid phase in which at least one catalyst is suspended. Frequently, the system will also include a gas phase from which the reactants are dissolved into the liquid phase. Typical reactions of this type are oxidations and hydrogenations. The hydrogenation of hydrodehydrolinalool to give hydrolinalool and further to give tetrahydrolinalool is described. In this reaction sequence, the triple bond is first hydrogenated to give a double bond and finally to give a single bond. Selective hydrogenation of a carbonyl function of α,β-unsaturated carbonyl compounds is not described.

Batchwise processes in stirred-tank reactors are sometimes very expensive, lengthy (a reaction cycle consists of a preparation time for reactants and catalyst, the setting of the reaction conditions [pressure and temperature], the actual reaction time, followed by cooling and depressurization of the reactors and the removal and return of the catalysts) and personnel-intensive, and are more suitable for the preparation of small quantitities. When used for large quantities, this method leads to very large reaction apparatus and very long reaction times.

The use of continuous fixed bed reactors circumvents the batch operation, and is therefore more cost-effective and less personnel-intensive, but it has the major disadvantage that specially prepared catalysts have to be made and used in the fixed bed and can be exchanged or regenerated only by expensive means when activity is lost (very often, short on-stream times are observed), which in general leads to the entire plant being shut down, i.e. not only the hydrogenation stage, but also the following workup stage.

It is an object of the present invention to provide a robust, cost-effective process for the selective hydrogenation of the carbonyl function of α,β-unsaturated carbonyl compounds, in particular of citral to give geraniol and nerol, without the above-explained disadvantages while simultaneously providing improved space-time yields.

We have found that this object is achieved by a process for selective hydrogenation of olefinically unsaturated carbonyl compounds of the general formula I,

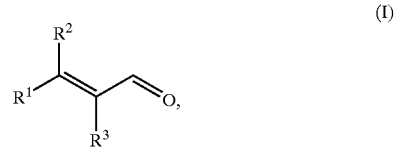

(I)

where
R$^1$ and R$^2$ are identical or different and are each independently hydrogen or a singly or multiply unsaturated straight chain or branched substituted or unsubstituted C$_1$–C$_{20}$-alkyl radical, an unsubstituted or substituted aryl radical or an unsubstituted or substituted heterocyclic group, and
R$^3$ is hydrogen or C$_1$–C$_4$-alkyl,
together with corresponding unsaturated alcohols of general formula II

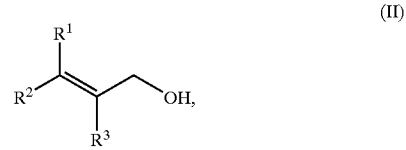

(II)

where R$^1$, R$^2$ and R$^3$ are each as defined above, in a reactor containing, in the absence or presence of a gas phase, a liquid phase holding at least one catalyst in suspension, which comprises passing the liquid phase and, if present, the gas phase through a device in the reactor having openings or channels whose hydraulic diameter is in the range from 0.5 to 20 mm.

The above reaction concerns the hydrogenation of an α,β-unsaturated carbonyl compound in which the carbonyl function is surprisingly hydrogenated with retention of the double bonds.

A singly or multiply unsaturated straight chain or branched C$_1$–C$_{10}$-alkyl radical is, unless otherwise stated, a methyl, ethyl, propyl, isopropyl, n-butyl, i-butyl, t-butyl, pentyl, hexyl, heptenyl, octyl, nonyl, decyl, 1-propenyl, 2-propenyl, 2-methyl-2-propenyl, 1-pentenyl, 1-methyl-2-pentenyl, isopropenyl, 1-butenyl, hexenyl, heptenyl, octenyl, nonenyl, or a decenyl radical, or the radicals corresponding to the compounds listed further below.

A C$_1$–C$_4$-alkyl radical is, unless otherwise stated, a methyl, ethyl, propyl, i-propyl, butyl or t-butyl radical.

An aryl radical is a benzyl, phenyl or naphthyl radical.

A heterocyclic group is, for example, a pyridine, pyrimidine, pyridazine, pyrazine, piperazine, imidazole, furan, oxazole, isothiazole, isoxazole, 1,2,3-triazole or 1,2,4-triazole, thiazole, thiophen or indole ring.

Substituents can be methyl, ethyl, propyl, i-propyl, butyl, t-butyl, fluorine, chlorine, bromine, iodine, nitro or amino.

Olefinically unsaturated carbonyl compounds of the formula I are preferably α,β-unsaturated carbonyl compounds, for example acrolein, methacrolein, crotonaldehyde, prenal, farnesal or citral, particularly preferably citral.

A preferred embodiment of the process involves the conversion of citral to give a mixture of geraniol and nerol.

The hydrogenation is carried out in a reactor according to EP 798 039, in which liquid and gas phases are passed through a device having openings or channels having a hydraulic diameter in the range from 0.5 to 20 mm, preferably 1 to 10 mm, particularly preferably 1 to 3 mm. The hydraulic diameter is defined as the quotient of 4 times the cross-sectional area of the opening and the circumference thereof.

The device having openings or channels that the reaction mixture is passed through can comprise a bed, a drawn-loop knit, an open-celled foam structure, preferably made of plastic (e.g. polyurethane or melamine resin) or ceramic, or a packing element as already known in principle, i.e. by its geometric form, from distillation and extraction technology.

Packing elements of this type, which offer the advantage of low pressure drop, are, for example, wire mesh packings. For the purposes of the present invention, however, the packings always have a hydraulic diameter that is considerably smaller, regularly by a factor of from 2 to 10, than comparable intervals in the field of distillation and extraction technology.

Wire fabric packings are particularly advantageous. This results from some of the suspended particles being retained by the fabric, and the relative velocity solid/liquid is improved considerably. Instead of fabric packings, packings made of other woven, loop-formingly knitted or felted liquid-permeable materials can also be used in the framework of the present invention. Further suitable packings include flat metal sheets, preferably without perforations or other large openings, for example corresponding to the types Montz B1 or Sulzer Mellapak. Packings made of expanded metal, such as packings of the type Montz BSH, are also advantageous. Openings, such as perforations, must again be kept correspondingly small in this case. The decisive factor for the suitability of packing in the framework of the present invention is not its geometry, but the opening sizes or channel widths available for flow in the packing.

Suspension reactors require the introduction of mechanical energy, which can be introduced, for example, through stirrers, jets or rising gas bubbles, in order to suspend the solid particles. However, an increase in the rate at which mechanical energy is introduced over and above the quantity necessary for suspension in the suspension reactors without internal fitments leads to no noticeable improvement in the material transfer between the liquid and suspended solid particles, since the achievable relative velocity only slightly exceeds the sedimentation velocity.

In order to increase this relative velocity, the use of catalyst particles having larger particle sizes (1 to 10 mm) has been suggested, in particular in moving and fluidized bed processes. Although these larger particles have the desired relative velocity relative to the surrounding liquid, their lower surface area based on volume, on the other hand, limits the conversion. The effects frequently cancel each other out, so that the problem of increasing the mass transfer is not solved.

High relative velocities can only be achieved when the suspension method is abandoned and fixed bed reactors are used, which, however, results in the abovementioned disadvantage of low catalyst surface area relative to volume becoming even more significant. Rather than using a bed of the catalyst in extruded or tableted form, metal sheets or fabrics can also be coated with the catalyst material that are in contact with the liquid or gas phase. A disadvantage of these reactors is, however, that the catalyst material can only be renewed by complete replacement of the coated materials in the event of contamination of the catalyst material by impure reaction products. This is expensive and leads, as is also the case in the use of fixed bed reactors, to expensive precautions, such as the ultrapurification of the starting materials.

In contrast to the prior art for the hydrogenation of α,β-unsaturated carbonyl compounds, in particular citral, an increased difference in the movements (high relative velocity) of the catalyst particles relative to the liquid phase in the area of the reaction is obtained in the inventive hydrogenation by the use of internal fitments in the bubble column reactors, because the particles are more strongly retained in the narrow openings and channels compared to the surrounding liquid. To obtain the suspension in the process of the invention, customarily available catalyst particles having an average particle size in the range from 0.0001 to 2 mm, preferably from 0.005 to 1 mm, particularly preferably from 0.001 to 0.1 mm, can be used. These particles lead to good results through their high surface areas based on volume. As a result, considerably higher space-time yields may be achieved.

The use of the hydrogenation of the invention thus results in high relative velocities of the liquid phase relative to the catalyst particles, which simultaneously have a high surface area based on volume.

The hydrogenation according to the present invention is carried out in a reactor having one of the above described internal fitments in the presence of a suspension catalyst and hydrogen at a pressure in the range from 1 to 100 bar, preferably 1 to 60 bar, particularly preferably 1 to 50 bar. The reaction temperatures are in the range from 40 to 120° C., preferably 60 to 100° C., particularly preferably 70 to 90° C.

In the process of the invention, for example, citral is not used in pure form, but as an aminic alcoholic solution. Suitable alcohols are preferably $C_1$–$C_4$-alcohols, suitable amine components are preferably tertiary $C_1$–$C_4$-amines. The concentration of citral in the solution is preferably in the range from 50 to 90% by weight, particularly preferably 60 to 80% by weight, the concentration of alcohol is in the range from 40 to 5% by weight, preferably 20 to 35% by weight, and the concentration of tertiary amine is in the range from 1 to 15% by weight, preferably 1 to 8% by weight.

The internal fitments used in the hydrogenation reactor are the fabric or sheet metal packings previously described. The reaction mixture, catalyst and hydrogen are circulated through the reactor at high velocity by pumping. The cross-sectional velocities of the gas and liquid phases are above 100 $m^3/m^2h$. The gas phase is mixed internally with the liquid phase by means of an injector nozzle.

The hydrogenation can be carried out using a commercially available suspension catalyst which contains at least ruthenium as the active component. As well as ruthenium, the catalyst can also comprise other active components, such as iron. The catalyst can be employed in metallic and/or oxide form with or without support. Suitable support materials include, for example, $SiO_2$, $TiO_2$, $ZrO_2$, $Al_2O_3$ or carbon in the form of graphite, carbon black or, particularly preferably, activated carbon. The ruthenium content is in the range from 0.1 to 10% by weight, the iron content in the range from 0.1 to 5% by weight, preferably from 0.5 to 1.5% by weight.

The hydrogenation of the invention can be carried out either continuously or batchwise, but the continuous process is preferred.

In the hydrogenation of the invention, in particular for the preparation of geraniol and nerol, the liquid is passed through the above-described device having openings and channels at a superficial velocity in the range from about 50 to 300 $m^3/m^2h$, preferably 100 to 250 $m^3/m^2h$. When the gas phase is present, its superficial velocity is preferably from 50 to 300 $m^3/m^2h$, particularly preferably 100 to 250 $m^3/m^2h$.

The hydrogenation of the invention can be carried out in various reactor forms, such as jet nozzle reactors, bubble columns or multitube reactors. The above-recited internal fitments preferably do not necessarily fill the entire reactor. The reactor according to the invention is preferably a vertical bubble column, which is preferably operated with upward cocurrent flow when a gas phase is present. A further preferred reactor is a heatable and coolable multitube reactor, in which the internal fitments of the invention are accommodated in the individual tubes. The suspended catalyst material can be introduced and removed again by means of conventional techniques (sedimentation, centrifugation, cake filtration, crossflow filtration).

For example, a reactor for the hydrogenation of a citral-containing solution to give a mixture of geraniol and nerol using an Ru/Fe-carbon suspension catalyst according to the present invention is described in detail with the aid of FIG. 1.

FIG. 1 shows, for example, the experimental construction of a continuously operated reactor (bubble column) 1 with packing 2, which is fed in through the pipes 3 with liquid and through the pipe 4 with fresh gas. The circulation gas 5 is mixed by means of the mixing jet 6 with fresh gas and the suspension 11 that is circulated by means of the pump 14. The reactor effluent is transferred through the pipe 7 into the separating vessel 8 where the gas phase is separated off and passed out through pipe 9. In order to limit the buildup of gaseous impurities, part of this gas flow is discharged through the pipe 10 and the remainder is passed into the reactor through the pipe 5. The suspended catalyst remains in the reactor system by being retained in the crossflow filter 12, only catalyst-free liquid phase exiting through pipe 13 for withdrawal. The temperature in the reactor system can be set as desired by means of the heat exchanger 15.

EXAMPLE 1

The reaction was carried out in a bubble column (3000 mm in length, 27.3 mm in diameter) equipped with a fabric packing according to the present invention. The experimental construction corresponded to FIG. 1. The geometry of the packing corresponded to a customarily available fabric packing of the type Montz A1 1200. The surface area of the packing relative to the volume was 1 200 $m^2/m^3$, which is based only on the surface area of the fabrics. The liquid containing the suspended catalyst and the gas were introduced into the packed reactor from below at a superficial velocity of 200 $m^3/m^2h$.

The reaction was carried out continuously at a hydrogen pressure of 22 bar and at 80° C. The catalyst used was an Ru/Fe-carbon suspension catalyst containing 5% of ruthenium and 1% of iron on activated carbon, which had an average particle size of around 50 $\mu m$.

The feed into the packed bubble column was a solution consisting of 70% by weight of citral, 27% by weight of methanol and 3% by weight of trimethylamine.

The conversion was 90% at a selectivity of >94% for geraniol and nerol and a citronellol selectivity of only 1.2%. The weight hourly space velocity was 3000 $g_{Citral}/(kg_{Cat}*h)$, and the space-time yield was 230 $kg_{Citral}/(m^3h)$.

EXAMPLE 2

The reaction was carried out in a bubble column (3000 mm in length, 27.3 mm in diameter) equipped with a fabric packing according to the present invention. The experimental construction corresponded to FIG. 1. The geometry of the packing corresponded to a customarily available fabric packing of the type Montz A1 1200. The surface area of the packing relative to the volume was 1 200 $m^2/m^3$, which is based only on the surface area of the mesh. The liquid containing the suspended catalyst and the gas were introduced into the packed reactor from below at a superficial velocity of 200 $m^3/m^2h$.

The reaction was carried out continuously at a hydrogen pressure of 30 bar and at 80° C. The catalyst used was an Ru/Fe-carbon suspension catalyst containing 5% of ruthenium and 1% of iron on activated carbon, which had an average particle size of around 50 $\mu m$.

The feed into the packed bubble column was a solution consisting of 70% by weight of citral, 27% by weight of methanol and 3% by weight of trimethylamine.

The conversion was 96% at a selectivity of >92% for geraniol and nerol and a citronellol selectivity of 4%. The weight hourly space velocity was 2 100 $g_{Citral}/(kg_{Cat}*h)$ and the space-time yield was 230 $kg_{Citral}/(m^3h)$.

We claim:

1. A process for selective hydrogenation of α,β-unsaturated carbonyl compounds of the general formula I

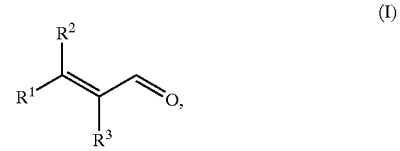

(I)

where
   $R^1$ and $R^2$ are identical or different and are each independently hydrogen or a singly or multiply unsaturated straight chain or branched substituted or unsubstituted $C_1$–$C_{20}$-alkyl radical, an unsubstituted or substituted aryl radical or an unsubstituted or substituted heterocyclic group, and
   $R^3$ is hydrogen or $C_1$–$C_4$-alkyl, together with corresponding unsaturated alcohols of general formula II

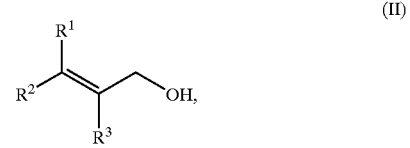

(II)

where $R^1$, $R^2$ and $R^3$ are each as defined above, in a reactor containing, in the absence or presence of a gas phase, a liquid phase holding at least one catalyst in suspension, which comprises passing the liquid phase and, if present, the gas phase through a device in the reactor having openings or channels whose hydraulic diameter is in the range from 0.5 to 20 mm.

2. The process as claimed in claim 1, wherein citral is hydrogenated to give a mixture of geraniol and nerol.

3. The process as claimed in claim 1, wherein the suspended catalyst particles have an average particle size in the range from 0.0001 to 2 mm.

4. The process as claimed in claim 1, wherein the device having openings or channels is a bed, a drawn-loop knit, an open-celled foam structure or a packing element as known in principle from distillation or extraction technology.

5. The process as claimed in claim 1, wherein the liquid phase and, if present, the gas phase are at least partly passed through openings or channels whose wall materials have surface roughness in the range from 0.1 to 10 times the average particle size of the suspended catalyst particles.

6. The process as claimed in claim 1, wherein the liquid phase is passed through the device having openings or channels at a superficial velocity in the range from 50 to 300 $m^3/m^2h$, and any gas phase present is passed through at a superficial velocity in the range from 5 to 300 $m^3/m^2h$.

7. The process as claimed in claim 1, wherein the citral is used as an aminic alcoholic solution.

8. The process as claimed in claim 1, wherein the concentration of citral in the solution is in the range from 50 to 90% by weight.

9. The process as claimed in claim 1, wherein the concentration of alcohol in the solution is in the range from 40 to 5% by weight.

10. The process as claimed in claim 1, wherein the concentration of amine in the solution is in the range from 1 to 15% by weight.

11. The process as claimed in claim 1, wherein the reactor is a bubble column.

* * * * *